United States Patent [19]

Kleiner et al.

[11] Patent Number: 4,474,711
[45] Date of Patent: Oct. 2, 1984

[54] PROCESS FOR THE PREPARATION OF MONOALKYL PHOSPHONITES

[75] Inventors: Hans-Jerg Kleiner, Kronberg; Horst-Dieter Thamm, Kelkheim, both of Fed. Rep. of Germany

[73] Assignee: Hoechst AG, Frankfurt am Main, Fed. Rep. of Germany

[21] Appl. No.: 443,132

[22] Filed: Nov. 19, 1982

[30] Foreign Application Priority Data

Nov. 21, 1981 [DE] Fed. Rep. of Germany ....... 3146197

[51] Int. Cl.$^3$ ................................................ C07F 9/48
[52] U.S. Cl. ..................................................... 260/978
[58] Field of Search ................................ 260/978, 962

[56] References Cited

U.S. PATENT DOCUMENTS 2,860,155 11/1958 Walsh .................................. 260/962
3,725,515 4/1973 Schimmelschmidt et al. ..... 260/978

OTHER PUBLICATIONS

Nifant'ev et al., "Zhurnal Obshchel Khimii", English Translation of vol. 42, No. 7, pp. 1460–1465, 1472–1475.
Houben–Weyl, Methoden der Organischen Chemie (=Methods of Organic Chemistry), vol. XII/1 (1963), p. 64.
Zeitschrift fur Anorganische und Allgemeine Chemie (=Journal of Inorganic and General Chemistry), vol. 399, (1973), p. 2.
G. M. Kosolapoff and J. S. Powell, J. Am. Chem. Soc. 72 (1950), p. 4291.
Soviet Inventors Certificate 172792, to E. E. Nifant'ev et al.
Chemical Abstracts, vol. 75, No. 23, Dec. 10, 1973, p. 410, Item 137424s.
Sovient Inventors Certificate 161748, to N. K. Blisnjuk et al.

Primary Examiner—Anton H. Sutto
Attorney, Agent, or Firm—Curtis, Morris & Safford

[57] ABSTRACT

Monoalkyl phosphonites are prepared by the esterification of phosphonous acids with alcohols at temperatures of about 125° to about 220° C., preferably of about 130° to about 180° C.

5 Claims, No Drawings

PROCESS FOR THE PREPARATION OF MONOALKYL PHOSPHONITES

Monoalkyl phosphonites are compounds of the general formula

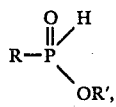

in which
R = an organic radical and
R' = an aliphatic radical.

They are mainly intermediates in various specialized fields, such as, for example, in the fields of flameproofing and plant protection, in the field of metal extraction agents and the like.

A number of different processes are known for their preparation. One of these known processes starts, for example, from dihalogenophosphines, especially from dichlorophosphines, which are reacted with alcohols according to the following equation (cf. German Offenlegungsschrift No. 2,519,192):

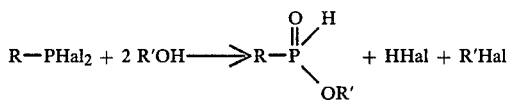

However, the formation of equimolar amounts of hydrogen halide and alkyl halide - especially the formation of the latter - as by-products is a disadvantage of this process.

The process for the direct esterification of free phosphonous acids with an alcohol, described by the Russian authors E.E. Nifant'ev, L.T. Elepina and V.N. Balakhontseva in Zh. Obsh. Khim. Volume 42, No. 7, pages 1,480–85, English Edition pages 1,472–75 (especially the experimental section on page 1,474), does not have this disadvantage. According to the only two examples published in this article, hexylphosphonous acid or nonylphosphonous acid is heated with butanol in p-xylene or toluene respectively, and the water of reaction formed is distilled off azeotropically. Since the binary azeotropes butanol/p-xylene, butanol/toluene and butanol/water boil at 116.2° C., 105.7° C. and about 92.5° C. respectively (at normal pressure; cf. Beilsteins Handbuch der organischen Chemie, 4th Edition, E III1, Springer Verlag 1964, page 1,489), the ternary azeotropes butanol/p-xylene/water or butanol/toluene/water can hardly boil above about 116° C. Supposedly, therefore, the reaction temperature can hardly be above about 120° C. at the most.

The yields in the publication by the abovementioned Russian authors are 72 and 55% of theory of distilled monobutyl hexylphosphonite and monobutyl nonylphosphonite respectively.

However, such yields are scarcely adequate, especially when carrying out the process on the industrial scale. It also seemed impossible to improve the yield by using a higher reaction temperature, for example, because it was then to be expected that an even higher proportion of the starting material (phosphonous acid) would disproportionate into the corresponding phosphonic acid and primary phosphane and would therefore be taken away from the desired reaction.

In fact, according to Houben-Weyl, Methoden der organischen Chemie (Methods of Organic Chemistry), Volume XII/1 (1963), page 64, phosphonous acid are supposed to disproportionate into the respective phosphonic acids and primary phosphanes at temperatures no higher than about 100° C., to an extent which increases with increasing temperature:

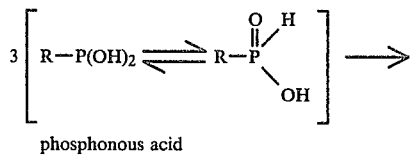

phosphonous acid

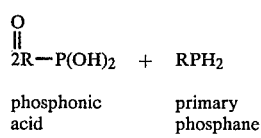

phosphonic acid    primary phosphane

In an attempt to improve the abovementioned process for the direct esterification of phosphonous acids with alcohols, especially in terms of increasing the yield of the corresponding monoalkyl phosphonites, it has now been found, surprisingly, that this object can be achieved precisely by using a higher reaction temperature - in complete contrast to what was to be expected on the basis of Houben-Weyl, loc. cit.

The subject of the invention is thus a process for the preparation of monoalkyl phosphonites by the esterification of phosphonous acids with alcohols, which comprises carrying out the esterification at temperatures of about 125 to about 220° C., preferably of about 130 to about 180° C.

Using this procedure, the yields of (distilled) monoalkyl phosphonites are in all cases about 90% of theory or above.

In principle, any possible phosphonous acids can be used as starting materials for the process. However, it is preferred to use those phosphonous acids of the formula

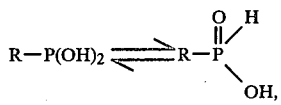

in which
R = $C_1$–$C_{18}$-alkyl, especially $C_1$–$C_4$-alkyl, $C_7$–$C_{12}$-aralkyl, especially benzyl, or $C_6$–$C_{10}$-aryl, especially phenyl.

Examples of phosphonous acids of this type are methylphosphonous, ethylphosphonous, butylphosphonous, octylphosphonous, eicosylphosphonous, benzylphosphonous and benzenephosphonous acids.

The phosphonous acids can in turn be obtained by the appropriate known methods. A preferred method of preparation is the hydrolysis of the corresponding dichlorophosphanes with water at temperatures of about 60 to about 100° C., preferably of about 80 to about 95° C., according to the process of application Ser. No. 443,133, filed Nov. 19, 1982.

Preferred alcohols for use in the esterification process according to the invention are those of the formula

R'OH, in which R'=C_4-C_{20}-alkyl, especially C_5-C_8-alkyl.

Examples of alcohols of this type are n-butanol, isobutanol, n-pentanol, 3-methylbutanol, n-hexanol, n-octanol, 2-ethylhexanol, n-dodecanol, n-octadecanol and the like. Of these alcohols, the primary alcohols are in turn preferred.

In principle, it is also possible to use mixtures of alcohols; in that case, however, corresponding mixtures of monoalkyl phosphonites are also obtained.

The alcohols are advantageously used in an excess of up to about 200%. Larger excesses are possible, but hardly advantageous.

To carry out the process according to the invention, the total amount of alcohol can be heated under reflux with the phosphonous acid; however, it is also possible to heat only part of the total amount of alcohol to the boil, whilst allowing a mixture of the phosphonous acid and the remainder of the alcohol to run in. On the other hand, it is also possible to heat the phosphonous acid with part of the alcohol, whilst allowing the remainder of the alcohol to run in. The water of reaction formed is advantageously removed azeotropically with the aid of a water separator, whilst the alcohol distilled off is continuously recycled into the process.

The reaction has ended when virtually no more significant amounts of water are separated off and when the acid number of the reaction mixture has reached a low constant value.

It can be advantageous - in particular when using higher-boiling alcohols - to carry out the reaction under reduced pressure and/or under an inert gas atmosphere; nitrogen, in particular, is a possible inert gas for this purpose.

When using low-boiling alcohols, it is also possible, if appropriate, to carry out the reaction under increased pressure for the purpose of ensuring that the relatively high reaction temperatures required according to the invention are maintained.

The reaction can be carried out either batchwise or continuously.

After the reaction has ended, working-up is carried out in a customary manner, preferably by distillation and, if appropriate, also by crystallization. The excess alcohols used in the process can be used again after they have been recovered by distillation. The distillation residues contain highly concentrated phosphonous acids, which can also be used again for the esterification process according to the invention.

The monoalkyl phosphonites prepared by this process with yields of, in all cases, about 90% of theory or above are of high purity and, in particular, free or virtually free of phosphane. The process therefore represents a considerable advance in this field.

The examples which now follow are intended to illustrate the invention in greater detail.

Example 1

320 g of methylphosphonous acid and 880 g of 3-methylbutan-1-ol are heated for 6 hours at 124–147° C., with stirring and under a nitrogen atmosphere. 71 g of water are simultaneously separated off over a 50 cm Vigreux silvered column with the aid of a water separator. A subsequent distillation gives 520 g of excess 3-methylbutan-1-ol containing 2% of bis-3-methylbutly ether. 546 g of mono-3-methylbutyl methylphosphonite, boiling point: 65 –66° C./0.08 kPa, are also obtained. This corresponds to a yield of 91% of theory. The distillation residue weighs 25 g and essentially consists of methylphosphonous acid or ester. It is free of the smell of phosphanes and can be used again.

Example 2

200 g of methylphosphonous acid and 440 g of n-pentanol are reacted for 6 hours at 134–163° C., the reaction being carried out as in Example 1. 340 g of n-pentyl methylphosphonite (boiling point: 75° C./0.1 kPa) are obtained in addition to re-usable excess n-pentanol. This corresponds to a yield of 91% of theory. The distillation residue weighs 20 g. It is free of the smell of phosphanes and can be used again.

Example 3

200 g of methylphosphonous acid and 650 g of 2-ethyl-hexan-1-ol are reacted for 3 hours at about 130 to 155° C., the reaction being carried out as in Example 1 but under reduced pressure (60–23.5 kPa). 457 g of 2-ethylhexyl methylphosphonite (boiling point: 92° /0.08 kPa) are obtained in addition to re-usable 2-ethyl-hexan-1-ol. This corresponds to a yield of about 95% of theory. The distillation residue is free of the smell of phosphanes and can be used again.

Example 4

212 g of ethylphosphonous acid and 500 g of 3-methylbutan-1-ol are reacted for 6 hours at 125–150° C., the reaction being carried out as in Example 1. 330 g of 3-methylbutyl ethylphosphonite (boiling point: 72° C. /0.13 kPa) are obtained in addition to re-usable excess 3-methylbutan-1-ol. This corresponds to a yield of 89% of theory. The distillation residue weighs 21 g. It is free of the smell of phosphanes and can be used again.

Example 5

100 g of benzenephosphonous acid and 155 g of 3-methylbutan-1-ol are reacted for 4.52 hours at 124–150° C., the reaction being carried out as in Example 1. 130 g of 3-methylbutyl benzenephosphonite (boiling point: 125° C./0.04 kPa) are obtained in addition to re-usable 3-methylbutan-1-ol. This corresponds to a yield of 90% of theory.

Example 6

97 g of benzenephosphonous acid and 66 g of isobutanol are reacted for 25 hours at 130–149° C., the reaction being carried out as in Example 1; at the same time, 36 g of isobutanol are slowly added dropwise, in portions, during this reaction period. 121 g of isobutyl benzenephosphonite (boiling point: 95–97° C./0.013 kPa) are obtained in addition to re-usable isobutanol. This corresponds to a yield of 90% of theory.

We claim:

1. In a process for the preparation of a monoalkyl phosphonite by the esterification of a phosphonous acid of the formula

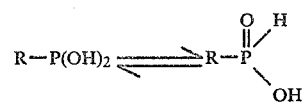

in which R is alkyl of from 1 to 4 carbon atoms, aralkyl of from 7 to 12 carbon atoms, or aryl of from 6 to 10 carbon atoms, with an alcohol of the formula

R'OH in which
R' is alkyl of from 4 to 20 carbon atoms, under an inert gas atmosphere, and wherein water formed in the esterification is separated off azeotropically,
the improvement which comprises carrying out the esterification at a temperature of from about 125 to about 220° C.

2. A process as defined in claim 1, wherein R is benzyl.

3. A process as defined in claim 1, wherein R is phenyl.

4. A process as defined in claim 1, which comprises carrying out the esterification at a temperature of from about 130 to about 180° C.

5. A process as defined in claim 1, in which R' is alkyl of from 5 to 8 carbon atoms.

* * * * *